(12) United States Patent
Benyo et al.

(10) Patent No.: US 12,128,187 B2
(45) Date of Patent: Oct. 29, 2024

(54) METHOD FOR REDUCING THE KINETOSIS EFFECT FOR PASSENGERS OF MOTOR VEHICLES OBSERVING AN IMAGE DISPLAYED ON A DISPLAY UNIT

(71) Applicants: thyssenkrupp Presta AG, Eschen (LI); thyssenkrupp AG, Essen (DE)

(72) Inventors: Imre Benyo, Budapest (HU); Richard Hirschmann, Mauren (LI)

(73) Assignees: thyssenkrupp Presta AG, Eschen (LI); thyssenkrupp AG, Essen (DE)

( * ) Notice: Subject to any disclaimer, the term of this patent is extended or adjusted under 35 U.S.C. 154(b) by 662 days.

(21) Appl. No.: 17/413,675

(22) PCT Filed: Jan. 7, 2020

(86) PCT No.: PCT/EP2020/050198
§ 371 (c)(1),
(2) Date: Jun. 14, 2021

(87) PCT Pub. No.: WO2020/144173
PCT Pub. Date: Jul. 16, 2020

(65) Prior Publication Data
US 2022/0062581 A1    Mar. 3, 2022

(30) Foreign Application Priority Data

Jan. 9, 2019   (DE) .................. 10 2019 100 379.2

(51) Int. Cl.
*A61M 21/02*    (2006.01)
*B60K 35/00*    (2024.01)
*A61M 21/00*    (2006.01)

(52) U.S. Cl.
CPC ............. *A61M 21/02* (2013.01); *B60K 35/00* (2013.01); *A61M 2021/005* (2013.01)

(58) Field of Classification Search
CPC ............ A61M 21/02; A61M 2021/005; A61M 21/00; A61M 2205/332; A61M 2205/507;
(Continued)

(56) References Cited

U.S. PATENT DOCUMENTS

2007/0198183 A1    8/2007   Morimoto
2009/0179987 A1    7/2009   Kim
(Continued)

FOREIGN PATENT DOCUMENTS

CN    106043302 A    10/2016
CN    107010075 A    8/2017
(Continued)

OTHER PUBLICATIONS

English Translation of International Search Report issued in PCT/EP2020/050198, dated Mar. 13, 2020.
(Continued)

*Primary Examiner* — Rodney A Butler
(74) *Attorney, Agent, or Firm* — thyssenkrupp North America, LLC

(57) ABSTRACT

A method can be utilized to reduce the kinetosis effect in passengers of motor vehicles having an autonomous and/or semi-autonomous driving mode. By means of a display unit, an image generated from image data is displayed to at least one passenger in a display area of the display unit while the motor vehicle is moving. The method may involve estimating a future change in an acceleration of the motor vehicle and modifying the image data based on the estimated future change in acceleration by way of a correction algorithm such that an effect of a relative movement between the displayed image and the passenger is reduced.

14 Claims, 2 Drawing Sheets

(58) Field of Classification Search
CPC ...... A61M 2230/63; A61B 5/18; B60K 35/00; G02B 2027/0183; G16H 30/40; G16H 40/63; G16H 20/70
See application file for complete search history.

(56) References Cited

U.S. PATENT DOCUMENTS

| | | |
|---|---|---|
| 2015/0120149 A1 | 4/2015 | Worrel |
| 2016/0297438 A1 | 10/2016 | Han |
| 2017/0158199 A1 | 6/2017 | Pallett et al. |
| 2020/0114929 A1* | 4/2020 | Wan ................. A61B 5/7435 |

FOREIGN PATENT DOCUMENTS

| | | |
|---|---|---|
| DE | 101 56 219 C | 8/2003 |
| DE | 10 2014 221 337 A | 4/2015 |
| DE | 10 2014 112 077 A | 2/2016 |
| DE | 10 2014 019 579 A | 6/2016 |
| EP | 2 228 089 A | 9/2010 |
| JP | H03-242436 A | 10/1991 |
| JP | 2009-093076 A | 4/2009 |
| JP | 2018-076027 A | 5/2018 |
| WO | 2005/080140 A | 9/2005 |

OTHER PUBLICATIONS

Sivak, Micheal et al., "Motion Sickness in Self-Driving Vehicles", University of Michigan Transportation Research Institute, (Apr. 2015).

* cited by examiner

METHOD FOR REDUCING THE KINETOSIS EFFECT FOR PASSENGERS OF MOTOR VEHICLES OBSERVING AN IMAGE DISPLAYED ON A DISPLAY UNIT

CROSS REFERENCE TO RELATED APPLICATIONS

This application is a U.S. National Stage Entry of International Patent Application Serial Number PCT/EP2020/050198, filed Jan. 7, 2020, which claims priority to German Patent Application No. DE 10 2019 100 379.2, filed Jan. 9, 2019, the entire contents of both of which are incorporated herein by reference.

FIELD

The present disclosure generally relates to methods for reducing the kinetosis effect in passengers of motor vehicles and to systems for operating display units.

BACKGROUND

In order to increase the driving safety of a motor vehicle in road traffic, modern motor vehicles have an increasing number of driver assistance systems aimed at increasing active safety. These driver assistance systems can enable an autonomous and/or semi-autonomous driving mode of the motor vehicle. In an autonomous driving mode, the motor vehicle can use various sensors of the driver assistance system to monitor the environment of the vehicle and control the vehicle completely automatically by setting predetermined values. In a semi-autonomous driving mode, on the other hand, the driver assistance system steers automatically by specifying a predetermined steering angle. This is the case, for example, with a semi-autonomous parking process. The driver assistance system takes over the steering of the motor vehicle and the driver operates the accelerator pedal and the brake.

In particular, in an autonomous driving mode, the driver may carry out activities other than the control of the motor vehicle. In order to check the condition of the motor vehicle, a display and operating unit may be provided which is permanently installed in the motor vehicle or which is located on a mobile device. When viewing and/or operating the display and operating unit while travelling, the driver or a front passenger may feel discomfort. So-called kinetosis (motion sickness) is caused by a conflict of sensory perceptions. The visual sense feels a substantial immobility of one's own body relative to the environment when looking at the display unit, while the sense of balance receives the constantly more or less changing accelerations to which the driver or a passenger is actually exposed. These contradictory perceptions regarding the position, movement and acceleration of one's own body lead to discomfort.

In DE 101 56 219 C1, image signals are provided for the passenger via optical reproduction devices while travelling, which are modified depending on driving-specific movement data in such a way that the visual impression of the observed images is correlated with the currently subjectively perceived position and movement values for the passenger. For this purpose, signals from motion and position sensors are evaluated by a data processing device and the image signals present in digital form are modified accordingly for reproduction. Driving-related changes in the position, for example, lead to corresponding changes in the image position during playback, and accelerations lead to a change in the image size.

Thus, a need exists for a method for reducing the kinetosis effect in passengers when viewing a display unit, which counteracts kinetosis disturbances and thus increases the driving comfort.

DETAILED DESCRIPTION

Figure 1:
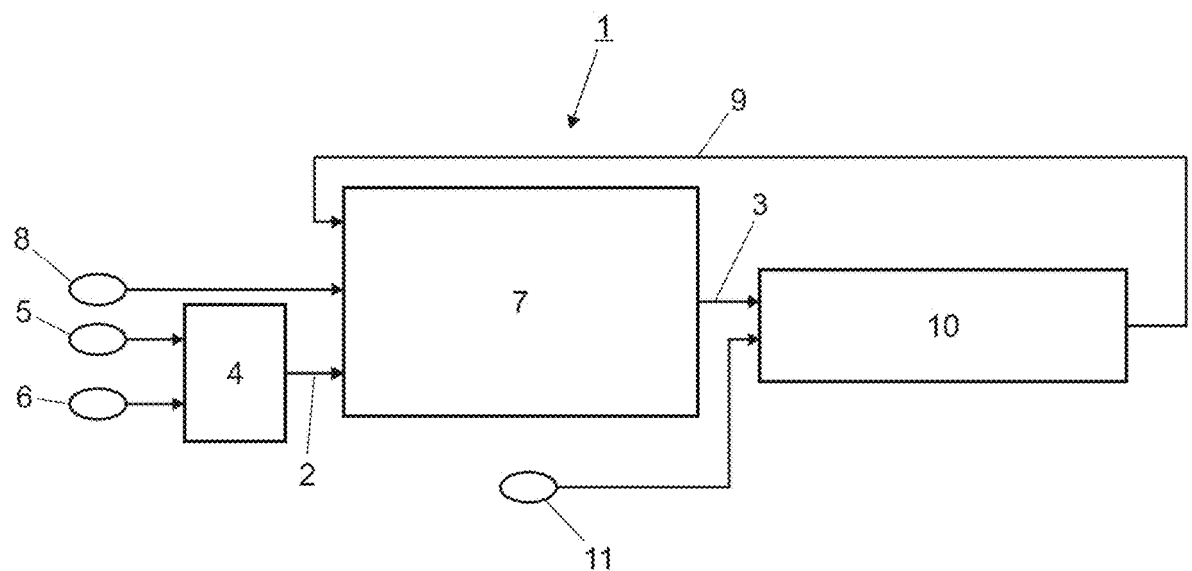
FIG. 1 is a schematic block diagram of a display of an example display unit adapted for motor vehicle acceleration.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

Accordingly, a method for reducing the kinetosis effect in passengers of motor vehicles having an autonomous and/or semi-autonomous driving mode is provided, wherein the at least one passenger is shown by a display unit an image generated from image data and displayed in a display area of the display unit while travelling, and the following steps are provided:

Estimating a future change in the acceleration of the motor vehicle;
Modifying the image data depending on the estimated future change in the acceleration of the motor vehicle by means of a correction algorithm in such a way that a relative movement between the image displayed and the at least one passenger is reduced.

Since the image data are adjusted based on an estimated future change in the acceleration of the vehicle, this is carried out before sensors would detect the change. Driving comfort is thus increased. The display unit can also be a combination of a display and control unit. Since the future change in acceleration is the cause of the relative motion, this can be reduced by modifying the image. The image data are thus dynamically adapted to the movement of the motor vehicle and are in equilibrium. The future change is estimated, for example, by using the position of the rack of the steering gear, a pedal position (gas demand, braking demand), or based on the ESP signal in emergencies.

Preferably, the correction algorithm is executed on a control unit within the motor vehicle, in particular on a control unit of an actuator, which provides the estimated future change of acceleration. The control circuit can therefore work particularly quickly since the necessary signals are immediately available to the algorithm and do not have to be requested via the vehicle network.

The acceleration is preferably a lateral acceleration and/or a longitudinal acceleration of the motor vehicle. The modification of the image data preferably includes enlargement, reduction, displacement or rotation of the displayed image, as well as combinations of these operations, wherein the different operations are assigned to individual accelerations. In this case, it is advantageous if the modification of the image data is carried out in such a way that a longitudinal acceleration in the direction of travel of the motor vehicle causes an enlargement and braking of the motor vehicle causes a reduction of the displayed image. Furthermore, it is advantageous when lateral accelerations cause lateral displacements and/or rotations of the displayed image.

In a preferred embodiment, the acceleration is a lateral acceleration estimated by a control unit of a steering system of the motor vehicle, wherein the estimate is made based on at least one of the parameters selected from the list of: deviation between actual position and target position of the actuator; motor vehicle speed; measured lateral acceleration. Preferably in this case, the control unit is an actuator control unit of a steering actuator. The previously mentioned position is then preferably the rack position of a rack-and-pinion steering gear. The measured lateral acceleration advantageously serves as a reference for the estimation, assuming that the friction between the motor vehicle wheel and the road surface does not change within a short period of time.

The correction algorithm preferably calculates a correction angle by which the image is rotated.

It may be generally intended to install the display unit fixedly in the motor vehicle or to use a mobile device which receives data from a vehicle network. It is advantageous if the image data provided for the mobile device for display are additionally adapted to the movement of the mobile device relative to the motor vehicle.

Furthermore, a system for operating a display unit is for use in a motor vehicle having an autonomous and/or semi-autonomous driving mode, wherein the system contains a display unit with a display area in which image data are displayed as an image, and a control unit, which is designed to estimate a future acceleration of the motor vehicle and depending on the signal to modify the image data in such a way that a relative movement between the depicted image and a passenger is reduced.

The above advantages result from the exploitation of the estimated future acceleration of the vehicle. In a preferred embodiment, the control unit is an actuator control unit of a steering actuator. In addition, a motor vehicle with a system for operating a previously described display device is provided, wherein the motor vehicle has an autonomous and/or semi-autonomous driving mode.

FIG. 1 shows a schematic representation of a first embodiment of a method for operating a display unit 1 for use in a motor vehicle. The display unit 1 comprises a display area in which image data 2 are displayed in an image 3. In this embodiment, the display unit 1 is virtual reality (VR) glasses. A processing unit 4 receives data from a camera 5 and data from an external source 6, for example a GPS sensor, from which a video is created in the processing unit 4. A control unit 7 of the VR glasses receives from the processing unit 4 the image data 2 as well as vehicle condition information 8 and data from a motion sensor 9, which detects a movement of the passenger (driver or front passenger) 10. A movement, in particular an acceleration, of the vehicle 11 is the cause of the movement of the passenger.

The control device 7 is designed to dynamically display the image data 2, depending on the movement of the vehicle and the passenger, within the display area on the display unit.

For this purpose, the image 3 viewed by the passenger is corrected in near real time, i.e. within a physiologically imperceptible time interval, with numerous parameters continuously mathematically corrected, wherein the direction and extent of this correction are controlled by the motion sensors 9, which continuously detect the movement of the passenger.

For example, during sharp cornering, the display of the image 3 in the display area is moved to the side, so that the relative movement between the image and the eyes is reduced for the viewer.

Figure 2:
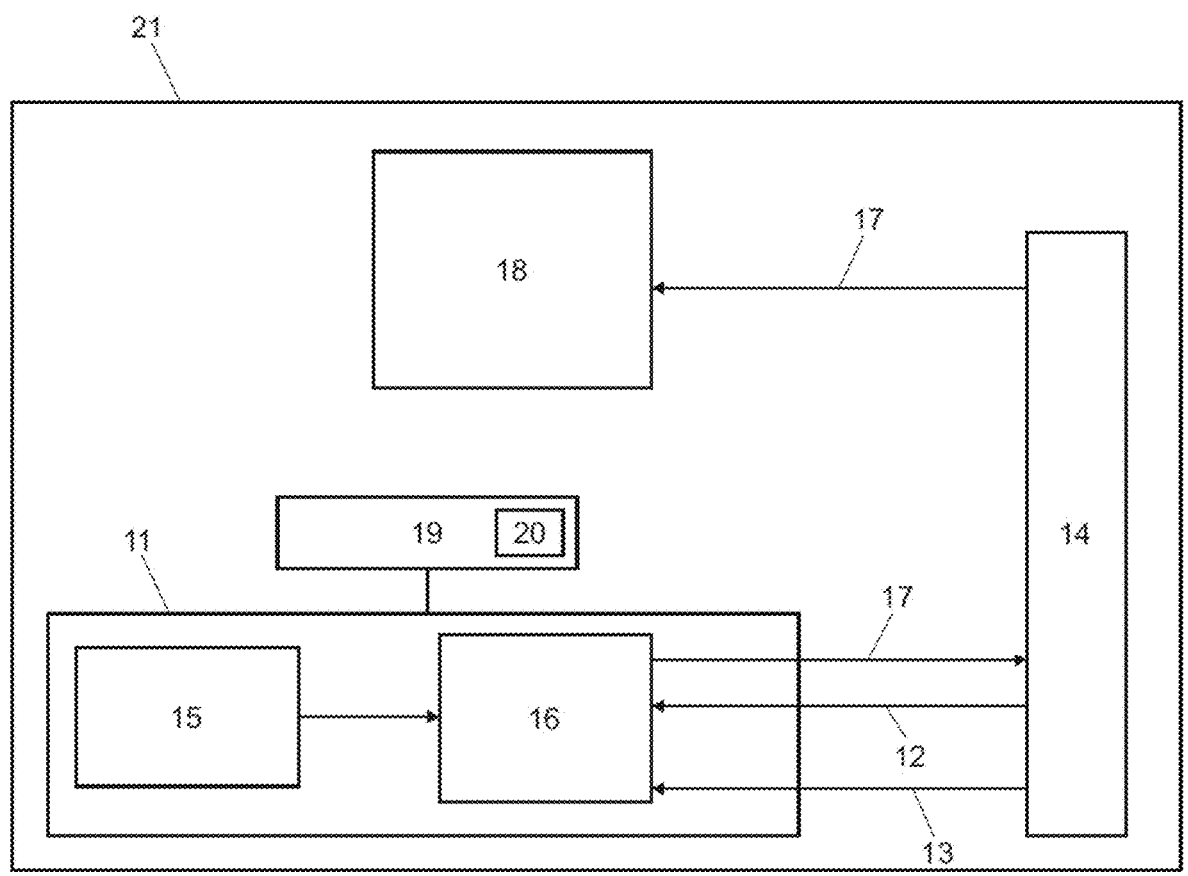
FIG. 2 is a schematic representing an example method for displaying a display unit adapted for motor vehicle acceleration by way of a correction angle.

FIG. 2 shows a schematic representation of a method for the adapted representation of image data. The actuators available in a motor vehicle (e.g. motor vehicle engine, brake or steering system) estimate a future change in the condition of the vehicle on the basis of the vehicle signals made available to them for control purposes. This may be, for example, a change in the acceleration of the motor vehicle. The actuators are able to detect a change in the acceleration by means of their estimators before an accelerometer actually measures them. This information is used in the present case to adapt the representation of the image data to the movement of the vehicle.

According to a possible embodiment, an actuator control unit 11 is shown, which is part of the steering of a motor vehicle 21, which also includes a steering actuator 19 and a control unit 20 of the steering actuator 19. The actuator acts indirectly on the motor vehicle wheels via a rack-and-pinion steering gear, as well as via tie rods and other components, causing the rack to shift transversely to the direction of travel to the right or left, whereby the wheels are pivoted around a respective pivot point.

The actuator control unit 11 receives the vehicle speed 12 and other reference signals, such as the measured lateral acceleration 13 or a similar sensor signal from the vehicle network 14. In addition, a deviation between the actual position and the target position of the actuator 15 is determined in the actuator control unit. In the present case this position may in particular be the rack position. The signals 12, 13, 15 serve as inputs into a correction algorithm 16. The lateral acceleration or the change thereof depends on the friction between the motor vehicle wheels and the road surface. The correction algorithm 16 therefore uses the lateral acceleration as a reference and estimates therefrom the change of the lateral acceleration on the assumption that the friction does not change within a short period of time. The reference value is updated regularly here. A correction angle 17 for the image data is calculated from the estimated future change of the lateral acceleration. This correction angle 17 is transmitted via the vehicle network 14 to a display unit 18, which calculates the adapted image data from it. The display unit 18 comprises a display area in which the adapted image data are displayed as an image. The image data are rotated around a center point with the correction angle. This rotation acts in the direction of lateral acceleration to reduce the relative movement between the passenger and the image shown.

The display unit 18 can be a device permanently installed in the car (for example a video display and/or a head-up display) and/or a mobile device (for example VR glasses and/or a smartphone). Fixed display units receive the correction angle 17 directly via the vehicle network 14. Mobile devices, on the other hand, have access to the correction information via a wireless connection. In the case of mobile devices, the image data are preferably additionally adapted to the movement of the mobile device relative to the motor vehicle. A motion sensor integrated in the mobile device provides the necessary motion information.

The method for correcting the image data works regardless of the type of acceleration. Here, only the correction for a lateral acceleration was presented as an example. A correction of the acceleration in the longitudinal direction is carried out analogously to this.

The correction algorithm can also be executed on another control unit within the motor vehicle. The advantage of using the actuator control unit is that the signals can be processed very quickly and that the control circuit is faster than with another control unit, which receives the necessary signals at low speed over the vehicle network.

The image data can be, for example, digitized films or video sequences. Text and/or a graphic can be displayed. Similarly, image information from the real driving environment can be generated by means of environment sensors and used as output data. Another option is the provision of interactive virtual or augmented environments (virtual reality (VR), augmented reality (AR)) as a data source. The passenger then does not move in front of a two-dimensional image as in the case of video/DVD, but in a three-dimensional environment, which is at least partially generated artificially and is adapted accordingly to the relative movement.

What is claimed is:

1. A method for reducing a kinetosis effect in a passenger of a motor vehicle that has an autonomous mode or semi-autonomous driving mode, wherein a display unit in the motor vehicle is configured to show an image generated from image data in a display area of the display unit while the motor vehicle is moving, the method comprising:
    estimating a future change in acceleration of the motor vehicle; and
    modifying the image data based on the estimated future change by way of a correction algorithm to reduce an effect of a relative movement between the image on the display unit and the passenger,
    wherein the acceleration of the motor vehicle is a lateral acceleration that is estimated by a control unit of a steering system of the motor vehicle, wherein the estimated future change is based on at least one of the following:
    a deviation between actual position and a target position of an actuator;
    speed of the motor vehicle; or
    measured lateral acceleration.

2. The method of claim 1 comprising executing the correction algorithm on a control unit within the motor vehicle.

3. The method of claim 2 wherein the estimated future change in acceleration is provided by the control unit of an actuator.

4. The method of claim 1 wherein modifying the image data comprises performing at least two of the following operations to the image on the display unit: enlarging, reducing, displacing, rotating.

5. The method of claim 1 wherein modifying the image data comprises performing at least one of the following operations to the image on the display unit: enlarging, reducing, displacing, or rotating, wherein the operations are assigned to different accelerations of the motor vehicle.

6. The method of claim 5 comprising:
    enlarging the image on the display unit based on a longitudinal acceleration in a direction of travel of the motor vehicle; or
    reducing the image on the display unit based on a longitudinal deceleration in a direction of travel of the motor vehicle.

7. The method of claim 5 comprising displacing or rotating the image on the display unit based on a lateral acceleration of the motor vehicle.

8. The method of claim 1 wherein the control unit is an actuator control unit of a steering actuator.

9. The method of claim 1 wherein the actual position is a rack position of a rack-and-pinion steering gear.

10. The method of claim 1 wherein the measured lateral acceleration serves as a reference for the estimated future change based on an assumption that friction between a motor vehicle wheel and a road surface will not change after a point in time when the lateral acceleration was measured.

11. The method of claim 1 wherein the correction algorithm calculates a correction angle by which the image is rotated.

12. The method of claim 1 wherein the display unit is permanently installed in the motor vehicle or is a mobile device that receives data from a vehicle network.

13. The method of claim 1 wherein the display unit is a mobile device that receives data from a vehicle network, wherein the method comprises adapting image data provided for the mobile device for display based on movement of the mobile device relative to the motor vehicle.

14. A system for operating a display unit in a motor vehicle that has an autonomous driving mode or a semi-autonomous driving mode, the system comprising:
    the display unit, which includes a display area in which image data are configured to be displayed as an image; and
    a control unit configured to estimate a future acceleration of the motor vehicle and modify the image data based on the estimated future acceleration to reduce an effect of a relative movement between the image on the display and a passenger;
    wherein the control unit is an actuator control unit of a steering actuator.

* * * * *